United States Patent [19]

della Valle et al.

[11] Patent Number: 4,639,437

[45] Date of Patent: Jan. 27, 1987

[54] KIT OR DEVICE AND METHOD FOR ADMINISTERING GANGLIOSIDES AND DERIVATIVES THEREOF BY INHALATION AND PHARMACEUTICAL COMPOSITIONS SUITABLE THEREFOR

[75] Inventors: Francesco della Valle, Padova; Aurelio Romeo, Rome, both of Italy

[73] Assignee: Fidia, S.p.A., Abano Terme, Italy

[21] Appl. No.: 599,340

[22] Filed: Apr. 12, 1984

[51] Int. Cl.$^4$ ............................................ A61K 31/70
[52] U.S. Cl. ........................................ 514/54; 514/53
[58] Field of Search ........................... 424/180, 45, 46; 536/17.2, 17.9, 53; 514/53, 54

[56] References Cited

U.S. PATENT DOCUMENTS

| 3,282,781 | 11/1966 | Macek et al. | 424/45 |
| 4,094,968 | 6/1978 | Hodson et al. | 424/46 |
| 4,476,119 | 10/1984 | della Valle et al. | 424/180 |

OTHER PUBLICATIONS

Ceccarelli et al., Effects of Brain Gangliosides on Functional Recovery in Experimental Regeneration and Reinnervation, Chem. Abs., 87:161751g (1976).
McCluer et al., Ganglioside Inner Esters, Advan. Exp. Med. Biol., 19, 95–102 (1972).
Gross et al., Identification of the Internal Acetal 5-Acetamido-2,7-Anhydro-3,5-Dideoxy-D-Glycero-D-Galacto-Nonulopyranose, Carbohydrate Research, 41, 344–50 (1975).
Gross et al., Formation of Ganglioside Internal Esters by Treatment with Trichloroacetic Acid–Phosphotungstic Acid Reagant, Chem. Abstracts, 87:129740s (1977).
Gross et al., Alkali-Labile, Sodium Borohydride-Reducible Ganglioside Sialic Acid Residues in Brain, J. Neurochem., 34(6), 1351–61 (1980).

*Primary Examiner*—Ethel G. Love
*Attorney, Agent, or Firm*—Birch, Stewart, Kolasch & Birch

[57] ABSTRACT

The present invention relates to a device or kit and a method for the inhalation administration of gangliosides and inner ester ganglioside derivatives useful for the treatment of various nervous disorders, such as those resulting from accidents or diseases which have damaged the nervous tissue.

10 Claims, No Drawings

KIT OR DEVICE AND METHOD FOR ADMINISTERING GANGLIOSIDES AND DERIVATIVES THEREOF BY INHALATION AND PHARMACEUTICAL COMPOSITIONS SUITABLE THEREFOR

BACKGROUND AND FIELD OF THE INVENTION

The present invention relates to a kit or device and a method for administering gangliosides or ganglioside derivatives by inhalation for therapeutic purposes and to pharmaceutical compositions suitable for such administration. The pharmaceutical preparations according to the present invention are used to treat disorders of the nervous system resulting from accidents or diseases which have in some way damaged the nervous tissue.

Gangliosides are a group of glycosphingolipids and have a structure containing a carbohydrate portion to which is linked a ceramide and a sialic acid moiety. The carbohydrate portion includes at least one galactose or glucose moiety and at least one N-acetylglucosamine or N-acetylgalactosamine moiety. The general structure of a ganglioside can thus be represented by the following formula:

one mole of a sialic acid { one mole of ceramide; at least one mole of galactose or glucose; at least one mole of N—acetyl-glucosamine or N—acetyl-galactosamine } where all of the moieties are linked by a glucosidic bond.

Numerous gangliosides have been identified and have been found to be particularly abundant in nerve tissue, especially in brain tissue. Various studies have shown that the most important of the sialic acids found in gangliosides are N-acetyl-neuraminic acid (NANA) and, to a lesser degree, N-glycolyneuraminic acid. Of the numerous gangliosides which have been identified, the following gangliosides, labeled by their international symbols, have been found to exist in significant amounts in ganglioside mixtures extracted from bovine brain tissue.

GD1b (16%)

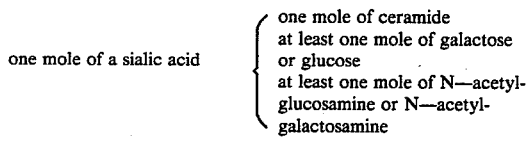

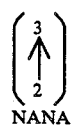

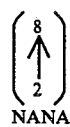

GT1b (19%)

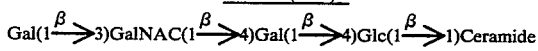

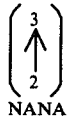

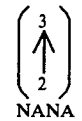

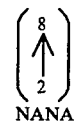

GM1 (21%)

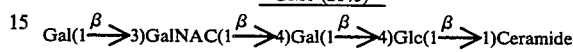

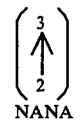

GD1a (40%)

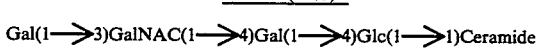

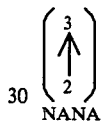

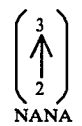

where Glc represents glucose, GalNAC represents N-acetylgalactosamine, Gal represents galactose, NANA represents N-acetyl-neuraminic acid and the percentages in parenthesis indicate the amount of each ganglioside found in the ganglioside mixture extracted from bovine brain tissue.

It is known that gangliosides play an important role in the nervous system and it has recently been demonstrated that gangliosides are useful in the treatment of disorders of the peripheral nervous system and pathologies of the central nervous system (Adv. Exp. Biol. 71, 275, (1976)); Brain Res. 197, 236, (1980)); Acta Otoryngol. 92, 433–437 (1981); Muscle and Nerve 2, 382–389 (1979); Neuroscience 8, (3) 417–429 (1983); Neuroscience Letters, 34, 1–5 (1982); Eur. J. Pharmacol. 80, 243–245 (1982); Experientia 37, 301–302 (1981); Muscle and Nerve 5, 107–110 (1982); Neurochem. Int. 4, (2–3) 167–174 (1982); Neuroscience 7, 495–499 (1982); Muscle and Nerve 5, 351–356 (1982); Acta Diabetol. Lat. 20, (3) 265–276 (1983); Rev. Clin. Esp. 168 (3) 193–198 (1983); Brain Res. 261, 163–166 (1983).

The therapeutic action of the gangliosides appears to consist mainly of stimulating sprouting phenomena in the nerve tissue and in activating the membrane enzymes involved in the conduction of nervous stimuli, such as the enzyme ($Na^+$, $K^+$) ATPase (Brain Res., 197, 236 (1980); J. of Neurochem., 37, 350 (1981)).

Nerve sprouting stimulated by the gangliosides will encourage restoration of the functioning of damaged nerve tissue.

Furthermore, it has been recently established that some ganglioside derivatives are more active than the gangliosides themselves in enhancing neuronal sprouting and in activating membrane enzymes implicated in the conduction of nervous stimuli, such as ($Na^+$, $K^+$) ATPase. These findings are the subject of applicant's co-pending applications Ser. No. 290,106, filed on Aug. 4, 1981, and Ser. No. 425,462, filed on Sept. 28, 1982, which are hereby expressly incorporated by reference. In particular, it has been established that inner ester derivatives of gangliosides are especially active in the treatment of nervous system disorders and are more active than the starting parent gangliosides. The inner ester derivatives of gangliosides are formed by the reaction between the carboxyl group of a sialic acid moiety with a hydroxyl group of one of the carbohydrate moieties or another adjoining sialic acid within the same ganglioside molecule (J. of Neurochemistry, 34, 1351 (1980); Bull. Mol. Biol. Med. 3, 170 (1978)).

For exemplary purposes, one possible inner ester derivative of a ganglioside could be represented by the following structure:

the carbohydrate moieties, specifically galactose. The formation of the inner ester bond, together with the normal glucosidic bond between the sialic acid and carbohydrate moiety, creates a lactonic ring, typically five or six-membered, characteristic of the structure of the inner ester ganglioside derivatives. While Formula I has been shown for exemplary purposes, it is to be noted that other lactonic rings having 5 or more membered ring structures could be formed as the sialic acid carboxyl group ester bonds with the hydroxyl group of a carbohydrate moiety.

As noted above, the inner ester ganglioside derivatives can also be formed when the carboxyl group of a sialic acid ester bonds to an adjoining sialic acid to which it is glucosidically bonded in the starting parent ganglioside. Such a structure could be represented by the following formula:

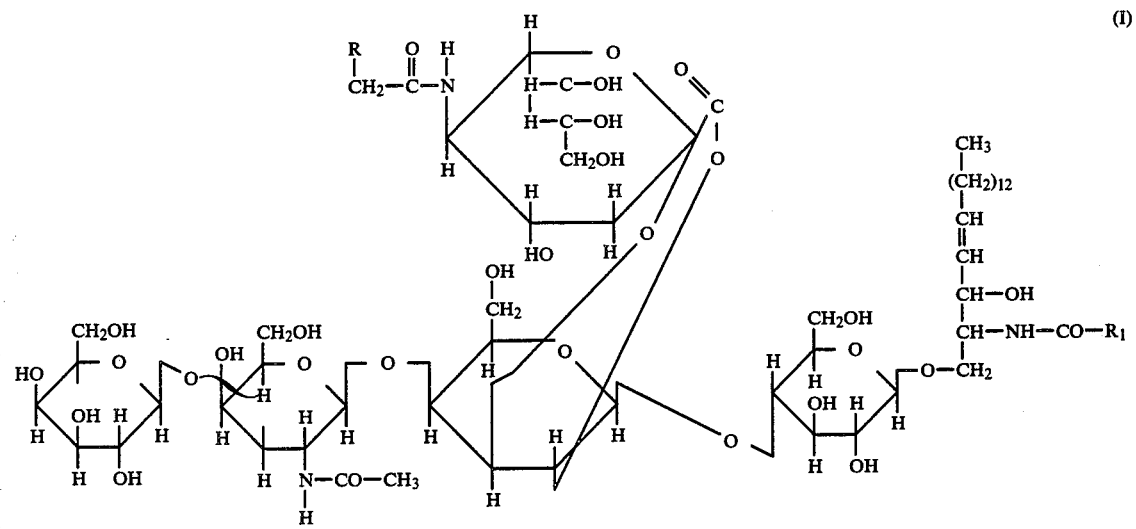

(I)

wherein R in the sialic acid moiety is H or OH and $R_1$ in the ceramide group is a fatty acid such as oleic, stearic or linoleic acid.

The inner ester ganglioside derivative (I) is an example of a derivative in which the carboxyl group of the sialic acid is ester bonded to a hydroxyl group of one of

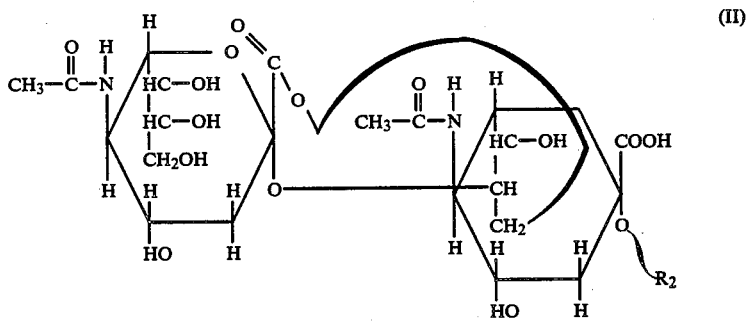

(II)

wherein $R_2$ represents the carbohydrate moiety which is glucosidically linked to the sialic acid moiety.

Another possible inner ester ganglioside derivative could be represented by the following formula:

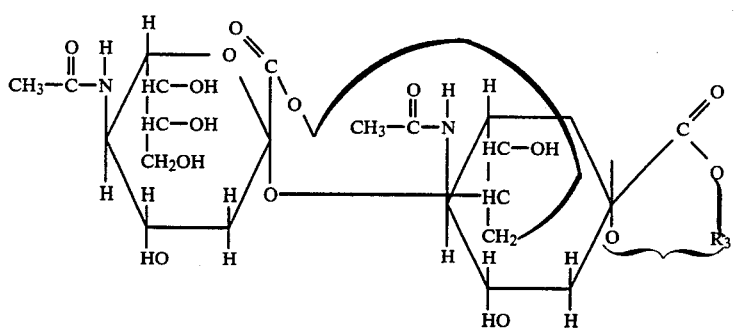

(III)

wherein $R_3$ represents the carbohydrate moiety to which the adjoining sialic acid is ester bonded. Formula III then represents an inner ester ganglioside derivative in which a sialic acid is ester bonded to an adjoining sialic acid which is itself ester bonded to a carbohydrate moiety. It is therefore evident that many variations of the above described derivatives could be formed, so that the inner ester derivatives of gangliosides are generally formed of a carbohydrate portion, at least one ceramide and at least one sialic acid moiety wherein one or more of the sialic acids are ester bonded to a carbohydrate moiety and/or one or more of the sialic acids are ester bonded to an adjoining sialic acid. Numerous inner ester derivatives of gangliosides are thus possible, of which the above described are shown for exemplary purposes only.

Some prior methods for the preparation of inner ester ganglioside derivatives include the following:

1. The formation of internal esters by simply allowing the gangliosides to stand in an acetic or trichloroacetic acid solution (Sphingolipids, Sphingolipidoses and Allied Disorders, Adv. Exp. Med. Biol. 19, 95, (1972); J. Neurochem. 28, 1133, (1977)).
2. The reaction of a water soluble carbodiimide with gangliosides in an aqueous medium (Carbohydr. Res. 41, 344, (1975)).
3. According to the process disclosed in applicant's above-noted co-pending applications inner ester ganglioside derivatives are prepared by reacting gangliosides with a lactonization reagent in a non-aqueous organic solvent under anhydrous conditions. Suitable organic solvents to be used in the reaction include dimethylsulfoxide (DMSO), dimethylformamide (DMF), sulfolane, tetrahydrofuran, dimethoxyethane and pyridine or mixtures thereof. Suitable lactonization reagents include carbodiimides soluble in organic solvents such as dicyclohexylcarbodiimide, benzylisopropylcarbodiimide and benzylethylcarbodiimide, 2-chloro-1-methyl-pyridinium salts, ethoxyacetylene and Woodward reagent (N-ethyl-5-phenyllisoxazolium-3'-sulfonate).

The inner ester ganglioside derivatives can be used as drugs for the therapy of different pathologies of the nervous system, particularly peripheral nerve and central nervous system disorders. More particularly, the inner ester ganglioside derivatives can be used in the treatment of peripheral nervous system disorders due to traumatic, compressive, degenerative or toxic-infectious causes where the stimulation of nerve regeneration and recovery of neuromuscular function is necessary, and in central nervous system disorders due to traumatic, anoxic, degenerative or toxic-infectious causes where the stimulation of neuronal sprouting is necessary for functional recovery. These disorders have previously been treated by the use of gangliosides; however, the inner ester derivatives of gangliosides have much greater activity than that of the gangliosides themselves.

It has been determined that gangliosides and derivatives thereof act systemically. Accordingly, the compounds discussed above either as a single ganglioside compound, or as a single ganglioside inner ester derivative as such or in the form of pharmaceutically acceptable salts, or as a mixture of gangliosides or derivatives thereof, may be administered systemically in order to obtain a therapeutic effect. This administration may be in the form of a pharmaceutical preparation intended for administration and can be administered in man or in animals by intramuscular, subcutaneous or intradermal routes, by means of injections, or by means of intravenous infusions. However, it has not previously been known that these compounds are able to reach the blood stream by penetrating the biological membranes of the respiratory system.

The object of the present invention is the discovery that the gangliosides, as such, or in the form of pharmaceutically acceptable salts, as well as ganglioside derivatives, either singly or in mixture, may be administered by inhalation and that these compounds are readily absorbed by this route to reach the blood stream.

DETAILED DESCRIPTION OF THE INVENTION

The present invention is specifically directed to the unexpected discovery that gangliosides and the inner ester derivatives thereof can be effectively and easily administered by inhalation. For such inhalation administration, the compounds are utilized in the form of pharmaceutical compositions such as those discussed hereinbelow.

According to the invention, a spray device can be utilized to administer the pharmaceutical compositions as aqueous solutions. Such a device would comprise a squeeze bottle or pump spray bottle adapted for use as a nasal spray for inhalation administration of the composition.

Alternatively, pressurized spray bottles can be utilized to administer the composition in the form of a suspension or solution of the active components together with conventional liquid propellants.

In addition, a kit or device for powder inhalation can be utilized whereby the pharmaceutical composition is prepared as a powder in a breakable capsule. For administration of the powder, the capsule is broken or a hole is formed therein, such as by an impact device or by hand, and the powder in the capsule is inhaled. Compositions for such powder inhalation will comprise a ganglioside compound or an inner ester ganglioside derivative in a solid form mixed with suitable pharmaceutically acceptable excipients or diluents, such as lactose.

For each of the above described devices for inhalation administration, the pharmaceutical composition will comprise as the active ingredient at least one ganglioside compound or at least one inner ester ganglioside derivative, or mixtures thereof, wherein the compounds may be present as a pharmaceutically acceptable salt thereof. The pharmaceutical composition for inhalation administration may also contain other active ingredients which are per se known, such as bronchodilators, to act against problems such as bronchoconstriction which is associated with powder inhalation in some patients. For this purpose, any bronchodilator may be used, such as adrenaline or isoprenaline, at an effective dose level.

EXAMPLE 1

The following examples represent pharmaceutical compositions containing as active ingredients single gangliosides or ganglioside mixtures for administration by inhalation:

| | |
|---|---|
| Composition a - (aerosol formulation) | |
| - ganglioside | 2% |
| - propellent mixture Freon 12 plus Freon 114 (60:40 w/w) | 98% |
| Composition b - (solid formulation) | |
| Each single dose contains: | |
| - ganglioside | 50 mg |
| - lactose | 20 mg |

EXAMPLE 2

The following examples represent pharmaceutical compositions containing as active ingredients gangliosides as sodium salts, alone or in mixture, for administration by inhalation.

| | |
|---|---|
| Composition a - (aerosol formulation) | |
| - ganglioside sodium salt | 2% |
| - propellent mixture Freon 12 plus Freon 114 (60:40 w/w) | 98% |
| Composition b - (aqueous spray formulation) | |
| - ganglioside sodium salt | 2% |
| - buffered aqueous solution pH 7 | 98% |
| Composition c - (solid formulation) | |
| Each single dose contains: | |
| - ganglioside sodium salt | 100 mg |
| - lactose | 15 mg |

EXAMPLE 3

The following examples represent pharmaceutical compositions containing as active ingredients inner ester derivatives of gangliosides alone or in mixture, for administration by inhalation.

| | |
|---|---|
| Composition a - (aerosol formulation) | |
| - ganglioside inner ester | 3% |
| - propellent mixture, Freon 12 plus Freon 114 (60:40 w/w) | 97% |

-continued

| | |
|---|---|
| Composition b - (solid formulation) | |
| Each single dose contains: | |
| - ganglioside inner ester | 75 mg |
| - lactose | 30 mg |

EXAMPLE 4

The following examples represent pharmaceutical compositions containing as active ingredients ganglioside sodium salts, alone or in mixture, and isoprenaline sulfate, for administration by inhalation.

| | |
|---|---|
| Composition a - (aerosol formulation) | |
| - ganglioside sodium salt | 2% |
| - isoprenaline sulfate | 0.1% |
| - propellent mixture, Freon 12 and Freon 114 (60:40 w/w) | 97.9% |
| Composition b - (solid formulation) | |
| Each single dose contains: | |
| - ganglioside sodium salt | 75 mg |
| - isoprenaline sulfate | 0.1 mg |
| - lactose | 25 mg |

PHARMACOLOGICAL PROPERTIES

The absorption of the ganglioside and ganglioside inner ester compounds has been demonstrated in experimental animals using techniques comprising the administration of an aqueous solution of the labeled active substance by means of tracheal intubation, by the nebulization, through tracheal intubation, of such aqueous solution, or by the atomization through tracheal intubation, of a dry powder mixture containing the active substances. Two animal species were used, i.e., rats and rabbits. The absorption was demonstrated by assaying for the presence of labeled active ingredient in blood over time.

MATERIALS AND METHODS

1. Substances used

(a) Labeled single ganglioside

Monosialotetrahexosylganglioside $GM_1$ labeled on the sphingosine moiety according to the method of Tettamanti et al. (in "Gangliosides in Neurological and Neuromuscular Function, Development and Repair" Eds. M. M. Rapport, A. Gorio, Raven Press. (N.Y.) 1981, p. 225–240) was used as a representative ganglioside molecule.

(b) Labeled ganglioside mixture

The ganglioside mixture used was similar to the natural mixture that is obtained by extraction and purification from bovine cerebral cortex. The mixture was made up by compounding the single ganglioside fractions in the following percent proportions:

monosialotetrahexosylganglioside $GM_1$: 21%
disialotetrahexosylganglioside $GD_{1a}$: 40%
disialotetrahexosylganglioside $GD_{1b}$: 17%
trisialotetrahexosylganglioside $GT_{1b}$: 19%

The monosialotetrahexosylganglioside $GM_1$ contained a $^3H$-label on sphingosine as specified under item (a) as a tracer for the mixture.

(c) Inner ester derivatives of labeled GM1

Labeled inner ester derivative of monosialoganglioside was obtained from monosialoganglioside labeled on the sphingosine moiety according to the method cited under item (a). The inner esterification procedure according to the method described in applicant's co-pending U.S. application Ser. No. 290,106, filed on Aug. 4, 1981, was used for this labeled ganglioside to obtain the labeled inner ester derivative.

Specifically, the inner ester derivatives can be prepared according to one of the following procedures:

PROCEDURE 1

A mixture of gangliosides is obtained by extraction from bovine brains and 5 g of this mixture are dissolved in 50 ml of DMSO. Then, 4 g of anhydrous styrene type resin (sulfonic acid) (50–100 mesh, H+ form) are added to the mixture and the resulting system is stirred for 30 minutes at room temperature. This treatment with an ion exchange resin converts all of the ganglioside carboxylate groups to —COOH (carboxyl) groups. Complete conversion of the carboxylate groups is confirmed by an appropriate physical analytical method, such as atomic absorption. The resin is then filtered under suction and the solution is treated with 1.5 g of dicyclohexylcarbodiimide and allowed to stand for one hour. The dicyclohexylurea which precipitates is removed by filtration and the remaining solution is treated with 100 ml of acetone causing precipitation of the product inner ester ganglioside derivatives. The method yields 4.6 g of inner ester product (about 90–95% of the theoretical value).

PROCEDURE 2

9 g of a ganglioside mixture (sodium salt) are dissolved in 80 ml of distilled water and passed through a column filled with 20 g of Dowex 50 w×8 (100–200 mesh triethylammonium form).

This product, anhydrified in high vacuum, is dissolved (with the aid of a sonicator bath) in 200 ml of anhydrous tetrahydrofuran containing 8 ml of triethylamine.

This solution is slowly added to 600 ml of anhydrous tetrahydrofuran (4 hours) containing 40 mM of 2-chloro-1-methyl-pyridinium salt (where the anion could be, for example, iodide, toluene-4-sulfonate, trifluoromethane sulfonate, etc.), under continuous stirring and maintaining a constant temperature of 45° C.

This reaction is carried out for 18 hours at 45° C.

The excess reagent is filtered off and the mixture is concentrated in a stream of nitrogen, the residue is redissolved in 90 ml of chloroform/methanol 1:1 and precipitated in 450 ml of acetone. The product is finally dried in high vacuum.

Yield—7.9 g (89.7% of the theoretical value).

PROCEDURE 3

8 g of $GM_1$ (sodium salt) are dissolved in 80 ml of distilled water and passed through a column filled with 10 g of Dowex 50 w×8 (100–200 mesh triethylammonium form).

This product, anhydrified in high vacuum, is dissolved (with the aid of a sonicator bath) in 200 ml triethylamine.

This solution is slowly added to 600 ml of anhydrous tetrahydrofuran (4 hours) containing 20 mM of 2-chloro-1-methyl-pyridinium salt (where the anion could be, for example, iodide, toluene-4-sulfonate, trifluoromethane sulfonate, etc.), under continuous stirring and maintaining a constant temperature of 45° C.

This reaction is carried out for 18 hours at 45° C.

The excess reagent is filtered off and the mixture is concentrated in a stream of nitrogen, the residue is redissolved in 80 ml of chloroform/methanol 1:1 and precipitated in 400 ml of acetone. The product is finally dried in high vacuum.

Yield—7.0 g (88.4% of the theoretical value).

PROCEDURE 4

9 g of a ganglioside mixture (sodium salt) are dissolved in 80 ml of distilled water and passed through a column filled with 20 g of Dowex 50 w×8 (100–200 mesh pyridinium form).

This product, anhydrified in high vacuum, is dissolved in 800 ml of anhydrous tetrahydrofuran and 4.2 g (60 mM) of ethoxyacetylene.

This mixture is refluxed for 3 hours, the refluxer is cooled at −10° C. and equipped with an anhydrifying valve.

After removing the solvents and excess of ethoxyacetylene, the residue is dissolved in 80 ml of chloroform/methanol 1:1 and precipitated in 400 ml of acetone.

Yield—8.1 g (92.0% of the theoretical value).

PROCEDURE 5

8 g of $GM_1$ (sodium salt) are dissolved in 80 ml of distilled water and passed through a column filled with 10 g of Dowex 50 w×8 (100–200 mesh pyridinium form).

This product, anhydrified in high vacuum, is dissolved in 800 ml of anhydrous tetrahydrofuran and 2.1 g (30 mM) of ethoxyacetylene.

This mixture is refluxed for 3 hours, the refluxer is cooled at −10° C. and equipped with an anhydrifying valve.

After removing the solvents and excess of ethoxyacetylene, the residue is dissolved in 80 ml of chloroform/methanol 1:1 and precipitated in 400 ml of acetone.

Yield—7.2 g (91.0% of the theoretical value).

PROCEDURE 6

9 g of ganglioside mixture (sodium salt) are dissolved in 80 ml of distilled water and passed through a column filled with 20 g of Dowex 50 w×8 (100–200 mesh pyridinium form).

This product, anhydrified in high vacuum and dissolved in 200 ml of anhydrous pyridine, is added to a suspension of 5.52 g (10 mM) of the Zwitterionic Woodward reagent (N-ethyl-t-phenylisoxazolium-3'-sulfonate, Woodward et al., J. Am. Chem. Soc. 83, 1010–1012, 1961) in 200 ml of anhydrous pyridine. This reaction mixture is stirred for 10 days at room temperature.

After filtration of the excess reagent and complete removal of the solvent, the residue is dissolved in 90 ml of chloroform/methanol 1:1 and precipitated in 450 ml of acetone.

Yield—7.2 g (81.8% of the theoretical value).

PROCEDURE 7

8 g of $GM_1$ (sodium salt) are dissolved in 80 ml of distilled water and passed through a column filled with 10 g of Dowex 50 w×8 (100–200 mesh pyridinium form).

This product, anhydrified in high vacuum and dissolved in 200 ml of anhydrous pyridine, is added to a suspension of 1.26 g (5 mM) of the Zwitterionic Woodward reagent (N-ethyl-t-phenylisoxazolium-3'-sulfonate), in 200 ml of anhydrous pyridine. This reaction mixture is stirred for 10 days at room temperature.

After filtration of the excess reagent and complete removal of the solvent, the residue is dissolved in 80 ml of chloroform/methanol 1:1 and precipitated in 400 ml of acetone.

Yield—6.3 g (79.5% of the theoretical value).

(d) Labeled mixture of ganglioside inner ester derivatives

The ganglioside inner ester mixture was obtained in a manner similar to that for the ganglioside mixture described under item (b) above, that is, by mixing in suitable proportions the single ganglioside inner ester derivatives obtained by the inner esterification method described in item (c) above. Specifically, the single ganglioside inner ester species were admixed in the following proprotions: 21% of the inner ester derivative of monosialoganglioside $GM_1$; 40% of the inner ester derivative of disialoganglioside $GD_{1a}$; 17% of the inner ester derivative of disialoganglioside $GT_{1b}$, and 19% of the inner ester derivative of trisialoganglioside $GT_{1b}$. The monosialoganglioside inner ester contained the species labeled on the sphingosine moiety, obtained as described under item (c) above, as a tracer of the mixture.

2. Methods of administration (a) Administration of an aqueous solution by tracheal intubation The administration of the aqueous solutions of the above described substances was carried out according to the method described in Enna and Schancher (Life Sci. 12, (1) 231–239, 1973) by intratracheal injection by means of a microsyringe of 50 mcl of the aqueous solution of the compounds under consideration.

(b) Administration of nebulized aqueous solutions by tracheal intubation

According to the method of Moss and Ritchie (Toxicol. Appl. Pharmacol. 17, 699–707, 1970) the solutions of the above described compounds were administered by means of tracheal cannula connected to a suitable nebulizer.

(c) Administration of atomized dry solid mixture by tracheal intubation

Very fine powders of the above described compounds were atomized intratracheally after weighing by means of a cannula according to the methods cited by Moss and Ritchie (Toxicol. Appl. Pharmacol. 17, 699–707, 1970).

3. Animal Species (a) Rats

For the pulmonary absorption experiments male Sprague Dawley rats, supplied by Charles River (Calco), weighinb between 200 and 250 grams, were used. The animals were treated according to the above described methods with 0.25 mg/kg bodyweight of each labeled compound.

After treatment the animals were housed in metabolic cages. Blood samples were obtained at 2-4-6-8 hours after treatment. The total radioactivity of the samples was counted by means of a Tricarb scintillator (Packard).

Male New Zealand rabbits weighing between 1.8 and 2.0 kg were treated as described under item (a) with the above described compounds.

RESULTS (a) Administration of an aqueous solution by tracheal intubation

The bioavailability of the compounds under examination after 5 hours from treatment, based on the calculation of the area under the plasma decrease curve, was found to be similar for the two animal species. Only very slight differences were noted between rats and rabbits. Therefore, the bioavailability of the compounds under examination was found to be comparable.

The results as shown in Table 1 are expressed in percentage over the intramuscular route taken as 100%.

(b) Administration of nebulized aqueous solutions by tracheal intubation

The bioavailability, also expressed in percentage over the intramuscular route taken as 100%, was found to again be similar for tracheal intubation of the two species and for the different compounds under examination. However, increased pulmonary absorption of the compounds after nebulization of the aqueous solutions was recorded (See Table 2).

(c) Administration of atomized dry solid mixture by tracheal intubation

It is apparent from the bioavailability calculations after administration of dry atomized powders that this method guarantees the best pulmonary absorption of the compounds under examination. Table 3 shows that the bioavailability 5 hours after inhalation administration is similar to the bioavailability observed after intramuscular injection.

TABLE 1

Bioavailability after 2 to 5 hours from the administration of 0.25 mg/kg by tracheal intubation. Aqueous solutions of the compounds under examination.

| Compounds Administered | Rat (Intramuscular route = 100) | Rabbit (Intramuscular route = 100) |
|---|---|---|
| Monosialoganglioside | 10.5 | 12 |
| Ganglioside Mixture | 9.8 | 11 |
| Monosialoganglioside inner ester | 12 | 11.5 |
| Ganglioside Mixture of inner esters | 10 | 11 |

TABLE 2

Bioavailability after 2 to 5 hours from the administration of 0.25 mg/kg by tracheal intubation. Nebulized aqueous solutions of the compounds under examination.

| Compounds Administered | Rat (Intramuscular route = 100) | Rabbit (Intramuscular route = 100) |
|---|---|---|
| Monosialoganglioside | 34 | 32 |
| Ganglioside mixture | 31 | 35 |
| Monosialoganglioside inner ester | 35 | 33.5 |
| Ganglioside mixture of inner esters | 31.8 | 33 |

TABLE 3

| Bioavailability after 5 hours from the administration of 0.25 mg/kg by tracheal intubation. Atomized dry powder of the compounds under examination. | | |
|---|---|---|
| Compounds Administered | Rat (Intramuscular route = 100) | Rabbit (Intramuscular route = 100) |
| Monosialoganglioside | 85 | 87 |
| Ganglioside Mixture | 88 | 88 |
| Monosialoganglioside inner ester | 80 | 85 |
| Ganglioside mixture of inner esters | 82 | 84 |

From the results reported above it can be seen that inhalation administration of gangliosides, inner ester ganglioside derivatives, or mixtures thereof provides good bioavailability of the compounds essentially comparable to that achieved by intramuscular administration. This discovery is unexpected since it was not heretofore known that these compounds were capable of reaching the blood stream by penetrating the biological membranes of the respiratory system.

This discovery is both unexpected and important because it shows that the compounds can be effectively and easily administered by inhalation using suspensions, solutions or solid powders of the compounds for use in liquid propellents or other pressurized or sprayable bottles. In this manner, the ganglioside compounds or derivatives thereof, particularly the inner ester derivatives, can be administered by a means which is safer, easier and more convenient than the previously used routes of injection or infusion. Individual patients can thereby administer the compounds themselves without the aid of medical personnel or other medical supplies.

Accordingly, the present invention provides a kit or device for inhalation administration whereby the ganglioside compounds or the inner ester derivatives thereof or mixtures thereof can be administered by means of a nasal spray device, a pressurized spray, or a capsule containing a powder for inhalation administration.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method for stimulating nerve sprouting which comprises administering by inhalation an effective amount of at least one ganglioside compound or a pharmaceutically acceptable salt thereof, or at least one inner ester ganglioside derivative or a pharmaceutically acceptable salt thereof, or mixtures thereof, wherein said inner ester ganglioside derivative comprises:

(a) a carbohydrate portion, at least one ceramide and at least one acid moiety;

(b) said carbohydrate portion including at least one N-acetylgalactosamine or N-acetylglucosamine moiety and at least one glucose or galactose moiety;

(c) said acid moiety including at least one N-acetylneuraminic acid or N-glycolylneuraminic acid; and (d) the carboxyl group of at least one of said acid moieties being ester bonded to a hydroxyl group of one of said carbohydrates or one of said acid moieties to form a lactonic ring.

2. The method of claim 1, wherein a single ganglioside compound or a pharmaceutically acceptable salt thereof is administered.

3. The method of claim 1, wherein a mixture of ganglioside compounds or pharmaceutically acceptable salts thereof is administered.

4. The method of claim 1, wherein a single inner ester ganglioside derivative or a pharmaceutically acceptable salt thereof is administered.

5. The method of claim 1, wherein a mixture of inner ester ganglioside derivatives, or pharmaceutically acceptable salts thereof, is administered.

6. The method of claim 1, wherein a mixture of at least one ganglioside compound or a pharmaceutically acceptable salt thereof and at least one inner ester ganglioside derivative or a pharmaceutically acceptable salt thereof is administered.

7. The method of claim 1, wherein said compounds are administered in the form of a nebulized aqueous solution.

8. The method of claim 1, wherein said compounds are administered in the form of a nebulized liquified propellent suspension or solution.

9. The method of claim 1, wherein said compounds are administered in the form of an atomized powder.

10. The method of claim 1, wherein in said inner ester ganglioside derivative each of said carboxyl groups of said acid moieties is ester bonded with a hydroxyl group of one of said carbohydrates or with one of said acid moieties to form lactonic rings.

* * * * *